(12) United States Patent
Wang et al.

(10) Patent No.: US 12,194,255 B2
(45) Date of Patent: Jan. 14, 2025

(54) EXPANDABLE-MOUTH CATHETER INTRODUCER TOOL

(71) Applicant: Covidien LP, Mansfield, MA (US)

(72) Inventors: Bin Wang, Irvine, CA (US); Eric Mintz, Newport Beach, CA (US)

(73) Assignee: Covidien LP, Mansfield, MA (US)

( * ) Notice: Subject to any disclaimer, the term of this patent is extended or adjusted under 35 U.S.C. 154(b) by 476 days.

(21) Appl. No.: 17/371,685

(22) Filed: Jul. 9, 2021

(65) Prior Publication Data
US 2023/0008013 A1    Jan. 12, 2023

(51) Int. Cl.
*A61M 25/06* (2006.01)
*A61M 25/00* (2006.01)
*A61M 25/10* (2013.01)

(52) U.S. Cl.
CPC .... *A61M 25/0662* (2013.01); *A61M 25/0074* (2013.01); *A61M 25/0668* (2013.01); *A61M 2025/0681* (2013.01); *A61M 2025/1081* (2013.01); *A61M 2209/04* (2013.01)

(58) Field of Classification Search
CPC .......... A61M 25/0074; A61M 25/0662; A61M 25/0668; A61M 2025/0681; A61M 2025/1081; A61M 2025/1065; A61M 25/0082; A61M 2025/0079; A61M 2025/0096; A61M 2025/0687; A61B 2017/22079; A61F 2/0103; A61F 2/0105; A61F 2/011; A61F 2002/016; A61F 2002/018
See application file for complete search history.

(56) References Cited

U.S. PATENT DOCUMENTS

| | | | | |
|---|---|---|---|---|
| 5,868,707 A | * | 2/1999 | Williams | A61M 25/1029 604/103 |
| 6,527,740 B1 | * | 3/2003 | Jackson | A61M 25/1038 604/103.05 |
| 10,321,933 B1 | * | 6/2019 | Ramee | A61M 39/06 |
| 10,532,185 B2 | | 1/2020 | Scarpine et al. | |
| 2004/0093005 A1 | * | 5/2004 | Durcan | A61M 25/10 606/194 |
| 2006/0264905 A1 | * | 11/2006 | Eskridge | A61M 25/0043 604/523 |

(Continued)

FOREIGN PATENT DOCUMENTS

| | | |
|---|---|---|
| EP | 1925332 A1 | 5/2008 |
| JP | 2018007877 A | 1/2018 |

OTHER PUBLICATIONS

Extended Search Report from counterpart European Application No. 22176037.4 dated Dec. 8, 2022, 8 pp.

*Primary Examiner* — Kami A Bosworth
(74) *Attorney, Agent, or Firm* — Shumaker & Sieffert, P.A.

(57) ABSTRACT

A medical assembly includes an expandable-mouth catheter and an introducer tool configured to facilitate advancement of the catheter into a delivery sheath. In some examples, a distal-most portion of the introducer tool includes a plurality of axial extensions separated by triangular-shaped slits. When the catheter is received within the introducer tool and when the introducer tool is received within a tapered portion of the delivery sheath, the axial extensions are configured to collapse radially inward to radially compress the expandable member and to enable the introducer to extend farther into the delivery sheath.

19 Claims, 6 Drawing Sheets

(56) References Cited

U.S. PATENT DOCUMENTS

| | | |
|---|---|---|
| 2007/0244440 A1 | 10/2007 | Pal et al. |
| 2007/0287885 A1* | 12/2007 | Brown ............... A61B 1/00142 |
| | | 600/107 |
| 2008/0146999 A1* | 6/2008 | Tanaka ................ A61M 25/104 |
| | | 604/96.01 |
| 2009/0069748 A1* | 3/2009 | Schaeffer .......... A61M 25/1006 |
| | | 604/103.09 |
| 2011/0144661 A1 | 6/2011 | Houser et al. |
| 2011/0208292 A1 | 8/2011 | Von Oepen et al. |
| 2011/0313404 A1 | 12/2011 | Amos et al. |
| 2012/0296313 A1* | 11/2012 | Andreacchi ........... A61M 39/06 |
| | | 604/509 |
| 2013/0090624 A1* | 4/2013 | Munsinger .............. A61F 2/962 |
| | | 604/103.05 |
| 2013/0096604 A1* | 4/2013 | Hanson ............... A61M 25/104 |
| | | 606/194 |
| 2013/0226276 A1 | 8/2013 | Newell et al. |
| 2013/0317589 A1 | 11/2013 | Martin et al. |
| 2015/0066127 A1 | 3/2015 | Johnson et al. |
| 2016/0089172 A1* | 3/2016 | Windheuser ........... A61B 17/22 |
| | | 606/115 |
| 2018/0236205 A1 | 8/2018 | Krautkremer et al. |
| 2019/0224448 A1* | 7/2019 | Connors ........... A61M 25/0662 |
| 2023/0001133 A1* | 1/2023 | Risch ..................... A61F 2/958 |
| 2023/0089857 A1* | 3/2023 | Griswold ............. A61M 25/10 |
| | | 604/103.05 |

* cited by examiner

_EXPANDABLE-MOUTH CATHETER INTRODUCER TOOL_

TECHNICAL FIELD

This disclosure relates to medical devices, such as catheters.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

This disclosure describes example introducer tools configured to facilitate introduction of a catheter into an inner lumen of a delivery sheath, as well as medical assemblies including a catheter and one or more introducer tools. In various examples described herein, introducer tools include a variable-diameter distal portion that reduces a pushing force required to introduce the catheter into a delivery sheath lumen of the delivery sheath. For instance, the distal portion of the introducer tool may be configured to collapse radially inward when in contact with an interior surface of the tapered portion of the sheath, thereby compressing the expandable member of the catheter retained therein, as well as enabling the introducer tool to advance farther into the lumen of the tapered portion of the sheath, as compared to other introducer tools lacking such a variable-diameter distal portion.

In this way, the introducer tool is configured to accommodate a varying inner diameter of a delivery sheath, e.g., by reducing or even eliminating a gap between an inner lumen of the introducer tool and an inner lumen of a reduced-diameter distal portion of the delivery sheath, thereby facilitating movement of the catheter between the inner lumens of the two devices when the catheter is received within the introducer tool and when the introducer tool is received within the delivery sheath. This disclosure also describes examples of methods of using the medical assemblies described herein.

In some examples, a medical assembly includes a catheter comprising an elongated catheter body and an expandable member located at a distal body portion of the elongated catheter body; and an introducer tool configured to facilitate introduction of the catheter into a sheath inner lumen of a delivery sheath, wherein the introducer tool defines a tool inner lumen configured to receive the expandable member, and wherein a distal tool portion of the introducer tool comprises a plurality of axial extensions configured to collapse radially inward toward a longitudinal axis of the introducer tool in response to a force applied by an interior surface of a tapered portion of the delivery sheath to the plurality of axial extensions.

In some examples, a medical device assembly includes a catheter comprising an expandable distal portion; and an introducer tool configured to facilitate introduction of the expandable distal portion of the catheter into a delivery sheath, wherein the catheter is positioned within an inner tool lumen of the introducer tool, and wherein the introducer tool comprises a plurality of axial extensions configured to collapse radially inward toward a longitudinal axis of the introducer tool in response to a force applied by an inner surface of the delivery sheath to an exterior surface of the plurality of axial extensions.

The examples described herein may be combined in any permutation or combination, as well as methods of using the medical devices and medical assemblies described herein.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
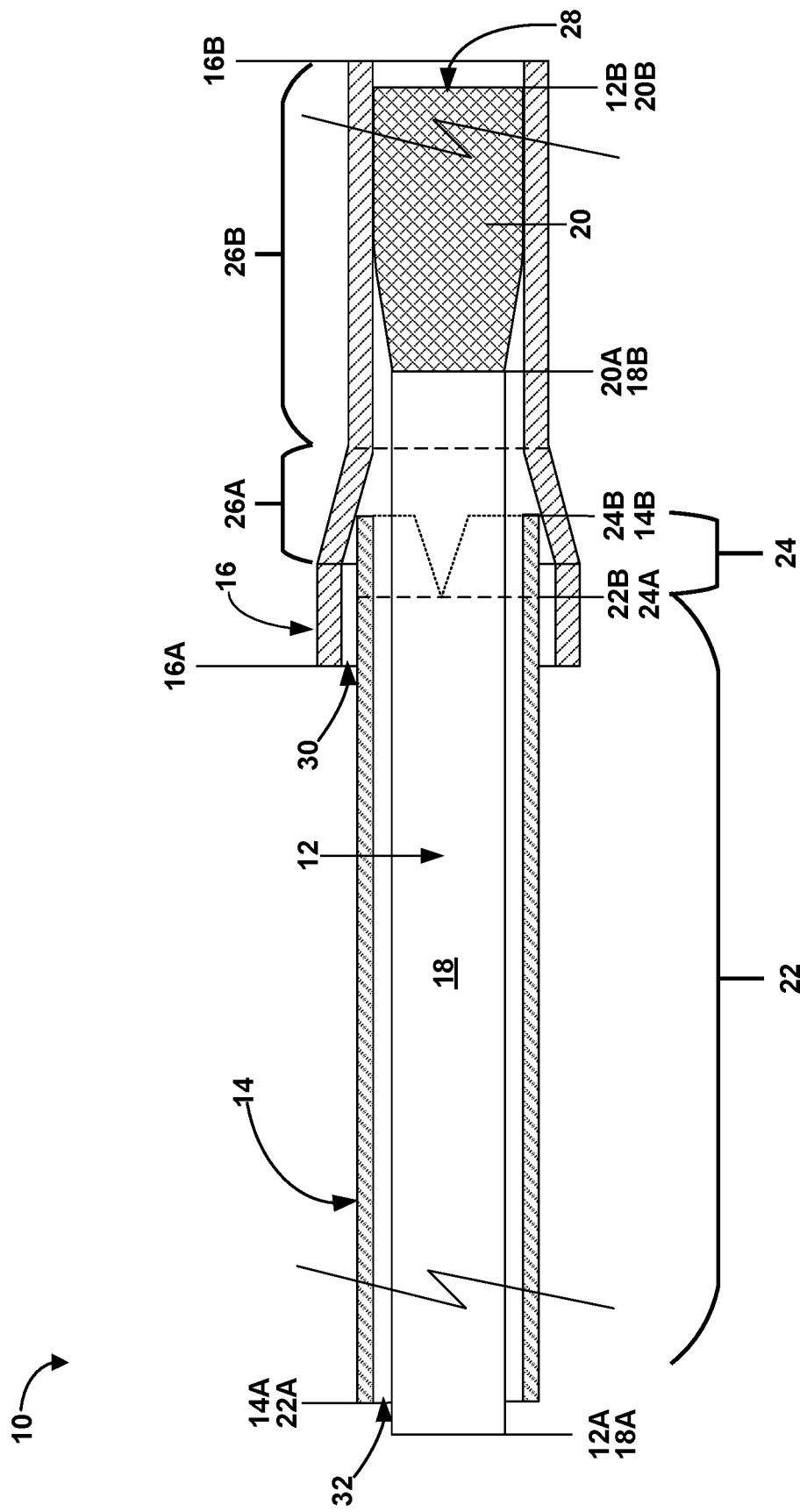
FIG. 1 is a conceptual cross-sectional view of an example medical assembly, which includes an expandable-mouth catheter and an introducer tool.

This disclosure describes variable-diameter introducer tools (also referred to herein as "compression tools") configured to facilitate introduction of an expandable-mouth catheter into an inner lumen of a delivery sheath, and medical assemblies one or more of the introducer tools and an expandable-mouth catheter. In various examples described herein, introducer tools of this disclosure include a variable-diameter distal portion that reduces a pushing force required to introduce the catheter into the delivery sheath inner lumen. For instance, the variable-diameter distal portion of the introducer tool may be configured to collapse radially inward when inserted into a tapered portion of the delivery sheath lumen, thereby enabling the introducer tool to extend farther into the tapered portion of the sheath lumen, as well as compressing an expandable member of the catheter retained within the introducer tool.

Example catheters described herein include a relatively flexible elongated body configured to be navigated through vasculature of a patient, e.g., tortuous vasculature in a brain of the patient. A distal portion (e.g., a distal tip) of the catheter includes an expandable member, such as an expandable stent-like structure or an expandable braid or other mesh-like structure, positioned at a distal portion of the elongated body. The expandable member is configured to expand radially outward within a hollow anatomical structure (e.g., a blood vessel) of the patient. This may enable, for example, the expandable member to engage with a thrombus, such as a clot, embolism, or other material such as plaques or foreign bodies, during an aspiration procedure, such as, but not limited to, a medical procedure using A Direct Aspiration first-Pass Technique (ADAPT) for acute stroke thrombectomy.

The expandable member may help improve aspiration of the thrombus into the catheter by providing a relatively large luminal diameter (and therefore exert a larger aspiration force against the thrombus or other material to be removed) and interior space for the thrombus to engage with the catheter compared to examples in which an otherwise similar catheter does not include an expandable member. In contrast, a catheter that does not include an expandable member may have more limited radial expansion and may thus make it harder to aspirate a thrombus (e.g., due to a smaller cross-sectional dimension of the distal end of the catheter). The expandable member may overcome such radial expansion limitations, thereby increasing thrombus engagement, reducing the amount of time required for revascularization, and increasing revascularization success rates for various procedures, as compared to similar procedures performed using catheters that do not include an expandable member to engage a thrombus.

Some expandable-mouth catheters may be limited in their potential use, e.g., with respect to the amount that the expandable member is able to expand, due to the relative difficulty of introducing larger-diameter catheters into a delivery sheath, e.g., an outer guide catheter or an introducer sheath. For instance, when the expandable member is advanced into the delivery sheath, the expandable member may impart an outward radial force onto an interior surface of a tapered portion of the sheath, which in some cases, may result in a significant frictional counterforce that impedes advancement of the catheter into a more-distal, reduced-diameter portion of sheath. Additionally, or alternatively, in some cases, the relatively soft, flexible distal portion (e.g., the expandable member) of the catheter may longitudinally deform or "bunch up" in response to a distal pushing force applied to the elongated body of the catheter and/or friction from the interior surface of the delivery sheath.

According to examples of this disclosure, an introducer tool includes a variable-diameter distal portion configured to reduce a pushing force required to introduce the catheter into the delivery-sheath inner lumen. For instance, the distal portion of the introducer tool may collapse radially inward when in contact with an interior surface of the tapered portion of the sheath, enabling the introducer tool to advance farther into the lumen of the tapered portion of the sheath, as compared to other introducer tools lacking such a variable-diameter distal portion.

In this way, the introducer tool is configured to reduce or even eliminate a gap between an inner lumen of the introducer tool and an inner lumen of a reduced-diameter distal portion of the delivery sheath, thereby facilitating a transfer of the catheter between the inner lumens of the two devices when the catheter is received within the introducer tool and when the introducer tool is received within the delivery sheath. As a result, the introducer tool may reduce an amount of force required to introduce the catheter into the delivery sheath, that would otherwise result from friction between the expandable member and the sheath.

FIG. 1 is a conceptual cross-sectional view of an example medical assembly 10 that includes at least an expandable-mouth catheter 12 and an introducer tool 14 configured to facilitate introduction of catheter 12 into a delivery sheath 16. As shown in FIG. 1, the catheter 12 (extending from the catheter proximal end 12A to the catheter distal end 12B) can include an elongated catheter body 18 (extending from the catheter body proximal end 18A to the catheter body distal end 18B) and an expandable member 20 (extending from the expandable member proximal end 20A to the expandable member distal end 20B). The introducer tool 14 (extending from the tool proximal end 14A to the tool distal end 14B) includes an elongated tool body 22 (extending from the tool body proximal end 22A to the tool body distal end 22B) and a collapsible (e.g., variable-diameter) distal tool portion 24 (extending from the collapsible tool portion proximal end 24A to the collapsible tool portion distal end 24B). The delivery sheath 16 (extending from the sheath proximal end 16A to the sheath distal end 16B) includes at least a tapered proximal sheath portion 26A and a reduced-diameter distal sheath portion 26B.

The catheter 12 is configured to be advanced through vasculature of a patient via a pushing force applied, e.g., to a proximal portion of the elongated catheter body 18 without buckling, kinking, or otherwise undesirably deforming (e.g., ovalization). The elongated catheter body 18 can include a plurality of concentric layers, such as an inner liner, an outer jacket, and a structural support member (e.g., a braid and/or a coil) positioned between at least a portion of the inner liner and at least a portion of the outer jacket.

The catheter 12 may be used as an aspiration catheter to remove a thrombus or other material from vasculature of a patient. A suction force (e.g., a vacuum) may be applied to the catheter proximal end 12A of the catheter 12 to draw a thrombus or other blockage into the distal catheter mouth 28. An aspiration catheter may be used in various medical procedures, such as a medical procedure to treat an ischemic insult, which may occur due to occlusion of a blood vessel (arterial or venous) that deprives brain tissue, heart tissue or other tissues of oxygen-carrying blood.

In some examples, the catheter 12 is configured to access relatively distal locations in a patient including, for example, the middle cerebral artery (MCA), internal carotid artery (ICA), the Circle of Willis, and tissue sites more distal than the MCA, ICA, and the Circle of Willis. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists or turns) through the vasculature to reach these tissue sites. Elongated catheter body 18 may be structurally configured to be relatively flexible, pushable, and relatively kink-resistant and buckle-resistant, so that it may resist buckling when a pushing force is applied to a relatively proximal section of the catheter 12 to advance elongated catheter body 18 distally through vasculature, and so that it may resist kinking when traversing around a tight turn in the vasculature. In some examples, the elongated catheter body 18 is configured to substantially conform to the curvature of the vasculature. In addition, in some examples, elongated catheter body 18 has a column strength and flexibility that allow at least distal portion of the elongated catheter body 18 to be navigated from a femoral artery, through the aorta of the patient, and into the intracranial vascular system of the patient, e.g., to reach a relatively distal treatment site. Alternatively, the elongated catheter body 18 can have a column strength (and/or be otherwise configured) to enable the distal portion to be navigated from a radial artery via an access site in the arm, e.g., at or near the wrist, through the aorta of the patient or otherwise to a common carotid or vertebral artery, and into the intracranial vascular system of the patient, e.g., to reach a relatively distal treatment site.

Although primarily described as being used to reach relatively distal vasculature sites, the catheter 12 may also be configured to be used with other target tissue sites. For example, the catheter 12 may be used to access tissue sites throughout the coronary and peripheral vasculature, the gastrointestinal tract, the urethra, ureters, fallopian tubes, veins, and other hollow anatomical structures of a patient.

The expandable member 20 is configured to radially expand within a blood vessel of a patient, e.g., to engage a thrombus within the vessel. The expandable member 20 is positioned at distal portion of (e.g., distal to) the elongated catheter body 18, such that a distal end 20B of the expandable member 20 defines the distal end 12B of the catheter 12 and a distal catheter mouth 28 open to an inner lumen of the catheter 12.

The expandable member 20 has any suitable configuration that enables it to expand radially outward from a compressed or delivery configuration to an expanded or deployed configuration, thereby expanding the distal catheter mouth 28 radially outward. In some examples, the expandable member 20 can include a frame configured to expand radially outward. For example, the expandable frame can enable the expandable member 20 to maintain its expanded shape (after it is expanded), even in the presence of a suction force applied to the inner lumen of the catheter 12 during an aspiration process. Example expandable frames include an expandable stent-like structure or an expandable tubular braid, weave, or other mesh-like configuration, which can each be formed from a plurality of structural elements. For example, each structural element can comprise a wire or filament. In some examples, the expandable member 20 may resemble a braided structure or mesh-like structure that includes a tubular body comprising a plurality of interwoven filaments. The filaments may be forced apart and radially outward from one another to increase the diameter at various portions of the expandable member 20.

In any of these examples, the expandable member 20 may include a flexible membrane coupled to (e.g., radially inward and/or radially outward of) the expandable frame or integrated into the expandable frame. In some examples, the flexible membrane may be formed of an elastomeric material, such as polyolefin thermoplastic elastomers, polyurethane elastomeric alloys, or silicone, that permits the expansion of the expandable member 20. The membrane can act as a fluid barrier in some examples. In other examples, the expandable member 20 does not include a flexible membrane.

The expandable member 20 is configured to compress into a delivery configuration for delivery through vasculature of a patient, e.g., through the delivery sheath 16, and expand radially outward within a blood vessel of a patient. This increased radial flexibility (e.g., range of expandability in a radial direction) may be useful, for example, when a relatively smaller delivery sheath 16 is required for insertion via certain vasculature access sites, such as the radial artery. As one non-limiting example, a radial-access sheath may have an inner diameter of about 5 French, as compared to about 6 French for femoral-access sheaths. Accordingly, a smaller-diameter (or other maximum cross-sectional dimension) catheter 12 may be useful for such applications.

In some examples, in its expanded states, the expandable member 20 defines a tubular, cylindrical, or funnel shape configured to provide the catheter 12 with a relatively large-diameter (or other maximum cross-sectional diameter) distal end 12B (compared to, for example, the proximal catheter end 12A) and an interior space for better engagement with a thrombus (e.g., clot or embolus). In some examples, the cross-section of the expandable member 20 in its expanded state may be round (e.g., circular) and the cross-sectional axis may be referred to as a diameter. In some examples, the cross-section may be irregularly shaped, in which case the cross-sectional dimension may be referred to as the major axis (e.g., a longest dimension of the cross-section). In the expanded configuration, the cross-section of the expandable member 20 may be wider at a distal end than a proximal end. For example, in the expanded configuration, the inner diameter at the distal end 20B of the expandable member 20 (e.g., at or near the distal catheter opening 28) may be about 150 percent to about 300 percent wider than an inner diameter of the expandable member 20 at or near the proximal end 20A of the expandable member 20.

The expandable member 20 can be configured to facilitate thrombus removal. In examples in which the catheter 12 is used with an aspiration procedure (e.g., ADAPT technique), the size and shape of the expandable member 20 may enable the catheter 12 to better engage a thrombus by increasing the distal catheter opening 28 into which the thrombus may be received, increasing the total aspiration force exerted on the thrombus via a larger luminal area, and/or by distributing the aspiration forces over a greater portion of the thrombus rather than a localized area, thereby allowing the thrombus to be aspirated into the catheter 12 more effectively. The expandable member 20 enables the catheter 12 to maintain a relatively small-diameter elongated catheter body 18 to facilitate navigability of the catheter 12, while also enabling the catheter 12 to exhibit improved engagement and suction force characteristics that may be attributed to having a large-diameter distal catheter end 12B. In some examples, the presence of the expandable member 20 may lead to improved revascularization success rates, such as due to the improved thrombus engagement and/or suction (e.g., to better pull the entirety of the thrombus into the catheter 12 during aspiration) as described herein.

In some examples, in the delivery configuration, a distal section of the expandable member 20 may have a cross-sectional dimension substantially equal to (e.g., equal to or nearly equal to) or only marginally greater than the outer diameter of the elongated catheter body 18 proximate to the expandable member 20. In some examples in which the expandable member 20 defines a tube shape or a cylinder shape (having an open distal catheter mouth 28) in an expanded (deployed) state, the expandable member 20 may define a substantially constant diameter (e.g., constant, or nearly constant in the absence of forces compressing the expandable member 20) along about 0.5 cm to about 3 cm, or 0.5 cm to about 2.5 cm of a length of the expandable member 20, which can be a distal-most length in some examples.

In some examples, the expandability of the expandable member 20 may enable the cross-sectional dimension of the elongated catheter body 18 to remain comparatively small. As described above, such a combination may enable the catheter 12 to exhibit the improved navigability characteristics of a catheter body with a small diameter while still providing the catheter 12 with the improved engagement and suction characteristics that may be attributed to having a large-diameter distal catheter end 12B.

The expandable member 20 may expand from a compressed (or "delivery") configuration to an expanded (or "deployed") configuration using any suitable technique. In some examples, the expandable member 20 may be configured to self-expand. For example, the expandable frame of the expandable member 20 may be formed from a metal and may include a shape-memory material such as Nitinol (and, optionally, additional material(s) or metal(s) such as radiopaque material(s) or metal(s)). In other examples, an electrical energy may be used to expand the expandable member 20. For example, the expandable member 20 (or a portion or a layer thereof) may be formed from a material or metal that bends or deflects in response to a current passed therethrough (or to heat generated as a result of such current). One such type of material is shape memory alloy actuator material, e.g., nitinol or Flexinol™ available from Dynalloy, Inc. of Irvine, Calif. USA.

The delivery sheath 16 may include an "outer" catheter, a "guide" catheter or any other suitable elongated body defining an inner sheath lumen 30 configured to receive the catheter 12 and define a passageway through which the catheter 12 can be navigated towards a target treatment site within the vasculature of the patient. As shown in FIG. 1, some delivery sheaths may define at least a tapered sheath portion 26A (e.g., that narrows along a distal direction), and a reduced-diameter (or "narrower") sheath portion 26B. The narrower sheath portion 26B may be positioned at and coupled to, a distal-most edge of the tapered sheath portion 26A, so as to define a continuous inner sheath lumen 30.

In some instances, some delivery sheaths may have different form factors than other delivery sheaths. For instance, the delivery sheath 16 may include dimensions (e.g., lengths, widths, thicknesses, inner/outer diameters, etc.) such that an introducer tool fits into or interacts differently with the delivery sheath 16 as compared to with other delivery sheaths. Thus, the example delivery sheath 16 shown in FIG. 1 is one example delivery sheath and is not intended to be limiting.

As described further below with respect to FIGS. 4A and 4B, when inserted into the inner sheath lumen 30 of the delivery sheath 16, an introducer tool 14 for the catheter 12 may contact an interior surface of the delivery sheath 16, such as within the tapered sheath portion 26A, which can prevent the introducer tool 14 from advancing farther into the inner sheath lumen 30. In addition, the contact with the tapered sheath portion 26A can result in an axial gap defined between a distal-most end of the introducer tool 14 and a proximal-most edge of the narrower distal sheath portion 26B of the delivery sheath 16. This axial gap may cause an increased amount of force to be required to advance the expandable member 20 of the catheter 12 outward from a distal mouth of the introducer tool 14 and into the inner lumen 30 of the narrower distal sheath portion 26B. For instance, the expandable member 20 of the catheter 12 may self-expand radially outward within this gap, into a partially expanded configuration having an outer diameter that is larger than the inner diameter of the inner sheath lumen 30 within the narrower distal sheath portion 26B. In these instances, advancing the catheter 12 distally forward into the narrower distal sheath portion 26B may require additional force to cause the expandable member 20 to neck back down into the delivery configuration in order to fit within the narrower distal sheath portion 26B, or in some instance, may cause deformation or "bunching up" of the expandable member 20 that inhibits the catheter 12 from advancing forward.

The medical assembly 10 further includes an introducer tool 14 configured to facilitate introduction of the catheter 12 into the delivery sheath 16. The introducer tool 14 includes a variable-diameter distal tool portion 24. In some examples, the distal tool portion 24 is configured to collapse radially inward to reduce the outer profile (e.g., an outer perimeter) of the introducer tool 14, enabling the introducer tool 14 to advance distally farther into an inner sheath lumen 30 of a tapered sheath portion 26A of the delivery sheath 16, as compared to examples in which an introducer tool having a non-tapering distal tool portion is used to introduce the catheter 12 into the delivery sheath 16. In this way, the introducer tool 14 may help reduce a pushing force required to introduce the catheter 12 into the delivery sheath 16. As detailed further below with respect to FIGS. 4A and 4B, advancing the introducer tool 14 farther into the inner sheath lumen 30 of the delivery sheath 16 may help reduce a pushing force required to distally advance the expandable member 20 of the catheter 12 from the inner tool lumen 32 into the inner sheath lumen 30.

In some examples, the medical assembly 10 may include a plurality of differently sized introducer tools. For instance, the catheter 12 may be packaged along with two or more introducer tools having different form factors, such as different lengths, diameters, ratios of the respective distal tool portion 24 to the rest of the elongated tool body 22, and the like. During use, a clinician may select a particular introducer tool from the plurality for use with a particular size of a delivery sheath 16. For instance, the clinician may select a desired size of a delivery sheath 16 based on, e.g., constraints of a procedure to be performed (e.g., an inner diameter of the vasculature receiving the delivery sheath 16), clinician preference, or other criteria.

Figure 2A:
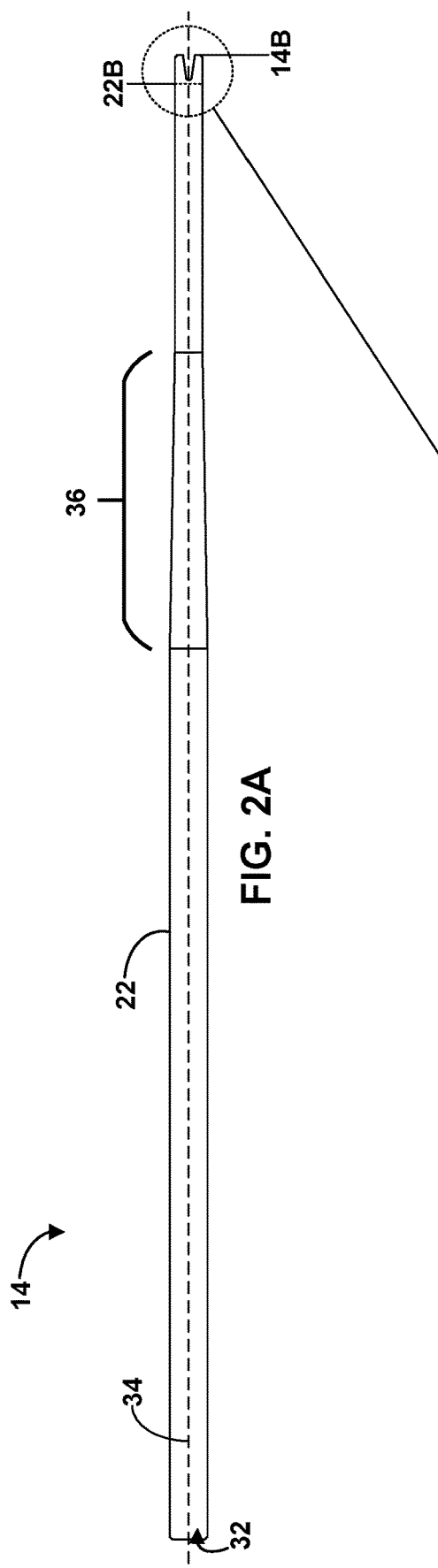
FIG. 2A is a side view of an example of the introducer tool of FIG. 1.

FIG. 2A is a side view illustrating an example of the introducer tool 14 of FIG. 1. As shown in FIG. 2A, the introducer tool 14 includes an elongated tool body 22, and a variable-diameter distal tool portion 24 at a distal portion of (e.g., distal to or defining a distal portion of) the elongated tool body 22. The elongated tool body 22 includes a hollow or tubular structure defining an inner tool lumen 32 configured to receive the expandable-mouth catheter 12 (FIG. 1). In some examples, the elongated tool body 22 includes a polymer tubing, such as, but not limited to, a high-density polyethylene (HDPE) tubing.

In some examples, the elongated tool body 22 and the distal tool portion 24 are configured to be removed from the catheter 12, e.g., to be split in a direction along a longitudinal axis 34 of the elongated tool body 22 and removed from around the catheter 12 in a lateral direction (orthogonal to a longitudinal axis of the catheter 12) after use. For example, in some cases, it may be advantageous for the introducer tool 14 to be configured to preferentially split along one or more predetermined paths. For example, the preferential splitting of the introducer tool 14 may enable a clinician to better predict how the introducer tool 14 will operate during use, which may allow the clinician to better orient the introducer tool 14 relative to the catheter 12 or the clinician during a medical procedure. In some examples, the introducer tool 14 is configured to preferentially split along one or more grooves defined by the tool body 22, the grooves defining the predetermined paths for the splitting of the tool body 22 into separate portions. The grooves reduce a thickness of an outer wall of the introducer tool 14, and, as a result, for a given outer wall thickness and material, a threshold amount of force needed to split the introducer tool 14 may be reduced relative to an introducer tool 14 that does not include such grooves. In some examples, the grooves may be formed during extrusion, via laser etching, selective chemical dissolution, or by using a mechanical cutting technique.

In some examples, the elongated tool body 22 defines a substantially uniform outer profile (e.g., circumference, diameter, perimeter, etc.), as measured along the longitudinal axis 34. In other examples, such as the example depicted in FIG. 2A, at least a tapered tool portion 36 of the elongated tool body 22 is tapered in a distal direction. In some examples, the tapered tool portion 36 may extend most or all of the length of the elongated tool body 22.

The distal tool portion 24 is located at a distal portion of elongated tool body 22 so as to form a distal-most portion of introducer tool 14. In some examples, but not all examples, the distal tool portion 24 includes a distal extension of the elongated tool body 22. For instance, the distal tool portion 24 may be integrally formed from the same material as the elongated tool body 22. In other examples, the distal tool portion 24 may be formed from a different material than the elongated tool body 22, and appended or adhered to the distal end 22B of the elongated tool body 22.

Figure 2B:
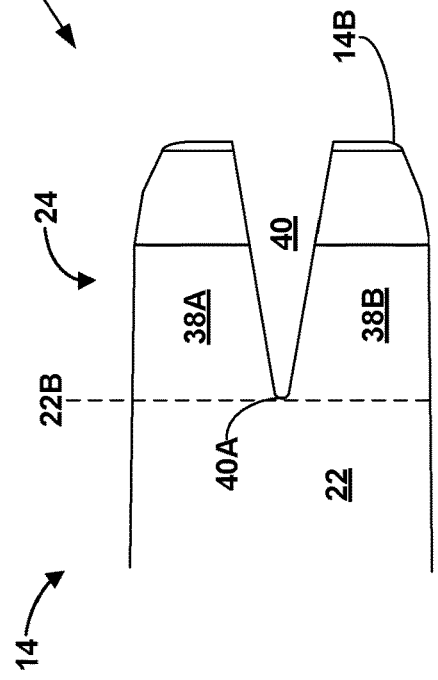
FIG. 2B is a side view of a variable-diameter distal portion of the introducer tool of FIG. 2A.

As shown in FIGS. 2A and 2B, in some examples, an exterior surface of the distal tool portion 24 (e.g., near the distal-most end 14B of the introducer tool 14) may define a curved, rounded, tapered or beveled shape as detailed further below. For instance, in examples in which both the elongated tool body 22 and the distal tool portion 24 are manufactured from, e.g., a common piece of extruded tubing, the tubing may be inserted into a machining tool comprising a die and mandrel. While inserted into the machining tool, the beveled exterior surface near the distal-most tool end 14B may form in response to heating, e.g., dielectric heating (also referred to as radio-frequency (RF) heating), of the introducer tool 14.

As detailed further below with respect to FIGS. 4A and 4B, the distal tool portion 24 is configured to collapse or compress radially inward to reduce the outer profile or perimeter of the distal-most portion of the introducer tool 14, in order to both compress expandable member 20 of catheter 12, and to enable the introducer tool 14 to extend distally farther into the delivery sheath 16. For instance, as shown in FIG. 2B, the distal tool portion 24 includes a plurality of axial extensions 38A, 38B (collectively, "axial extensions 38") that enable the introducer tool 14 to accommodate a varying inner diameter of the delivery sheath 16. The axial extensions 38 extend axially forward (e.g., in a distal direction) from the distal end 22B of the elongated body 22. In some examples, the axial extensions 38 may include portions of a tubular shape consistent with the shape of the distal end 22B of the elongated tool body 22. For instance, the axial extensions 38 may be distributed around a circumference of the distal tool portion 24, e.g., circumferentially around the longitudinal axis 34.

In the example depicted in FIGS. 1-4B, the distal tool portion 24 includes two axial extensions 38. In other examples, the distal tool portion 24 may include more than two axial extensions, such as three extensions, four extensions (e.g., as depicted in the example of FIGS. 5A and 5B), or more than four axial extensions.

Regardless of the number of axial extensions 38, each circumferentially consecutive pair of axial extensions 38 is circumferentially separated by a corresponding slit 40. That is, each axial extension 38 may be separated from a directly adjacent axial extension 38 by a slit 40. The slits 40 provide a space that enable the axial extensions 38 to collapse radially inward to reduce an outer perimeter of the distal tool portion 24 of the introducer tool 14. The axial extensions 38 may be formed using any suitable technique. For example, at the time of manufacture, the distal tool portion 24 may initially be formed as a coherent tubular or ring-shaped structure having a complete profile or outer perimeter, such as a circular circumference. During manufacture, two or more portions may be removed from the circumference of the circular-shaped structure, thereby forming the slits 40 (e.g., having the same shape as the removed portions), as well as defining each of axial extensions 38 therebetween.

The slits 40 may have any suitable shape. In the example depicted in FIG. 2B, the slit 40 is depicted as being generally triangular-prism shaped, extending axially (e.g., opening in a distal direction along the longitudinal axis 34) from a central angle located at a proximal-most slit edge 40A toward a distal-most end 14B of the introducer tool 14. As shown in FIG. 2B, the central angle at the proximal-most slit edge 40A may be rounded or beveled to facilitate the radially inward collapse of adjacent axial extensions 38.

Figure 3:
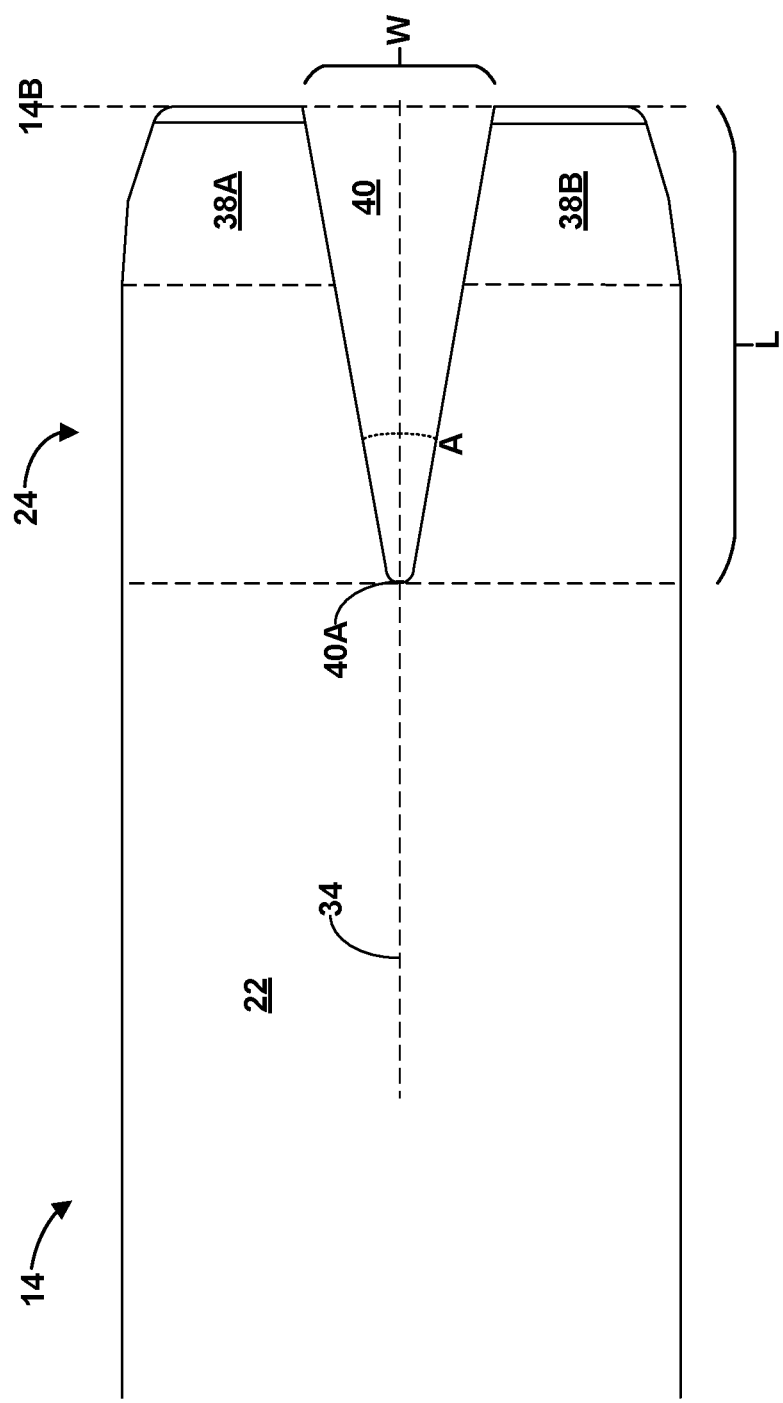
FIG. 3 is a diagram illustrating some example dimensions of the distal portion of the introducer tool shown in FIG. 2B.

FIG. 3 is diagram illustrating some example dimensions of the distal tool portion 24 of the introducer tool 14 shown in FIG. 2B. The dimensions shown and described with respect to FIG. 3 are merely illustrative, and are not intended to be limiting. For instance, the example dimensions shown in FIG. 3 may enable the distal tool portion 24 to collapse radially inward such that an outer profile of the distal tool portion 24 conforms to the interior surface of the tapered sheath portion 26A of a typical delivery sheath 16. As described above, dimensions of delivery sheaths (as well as expandable members 20 of catheters 12) may vary; accordingly, dimensions of the introducer tool 14 may vary as well.

In the example of FIG. 3, each axial extension 38 defines an axial length "L" measured along the longitudinal axis 34 from a proximal slit edge 40A of the slit 40 to a distal-most tool end 14B of the introducer tool 14. In some examples herein, the axial length "L" of the axial extensions 38 may be about 0.05 centimeters (cm) to about 1.00 cm, such as about 0.10 cm.

From the perspective shown in FIG. 3, the triangular-shaped slits 40 define a central angle "A" having a vertex at the proximal slit edge 40A and centered on (e.g., bifurcated by) the longitudinal axis 34. The angle "A" corresponds to a radial slit width "W" of the slits 40, and accordingly, an available space for the axial extensions 38 to collapse radially inward. For instance, a wider angle "A" enables the axial extensions 38 to collapse further inward, thereby reducing the outer profile or perimeter of the distal tool portion 24 while in the compressed configuration. In some examples herein, the angle "A" may be about 10 degrees to about 45 degrees, such as about 20 degrees.

From the perspective shown in FIG. 3, a distal-most edge of the triangular-shaped slits 40 define a radial slit width "W," as measured in a direction perpendicular to the longitudinal axis 34. Similar to the angle "A" defined above, the radial slit width "W" corresponds to an amount of available space for the axial extensions 38 to collapse radially inward. For instance, a wider radial slit width "W" enables the axial extensions 38 to collapse further inward, thereby reducing the outer profile or perimeter of the distal tool portion 24 while in the compressed configuration. In some examples herein, the radial slit width "W" may be about 0.02 cm to about 0.25 cm, such as about 0.04 cm.

Figure 4A:
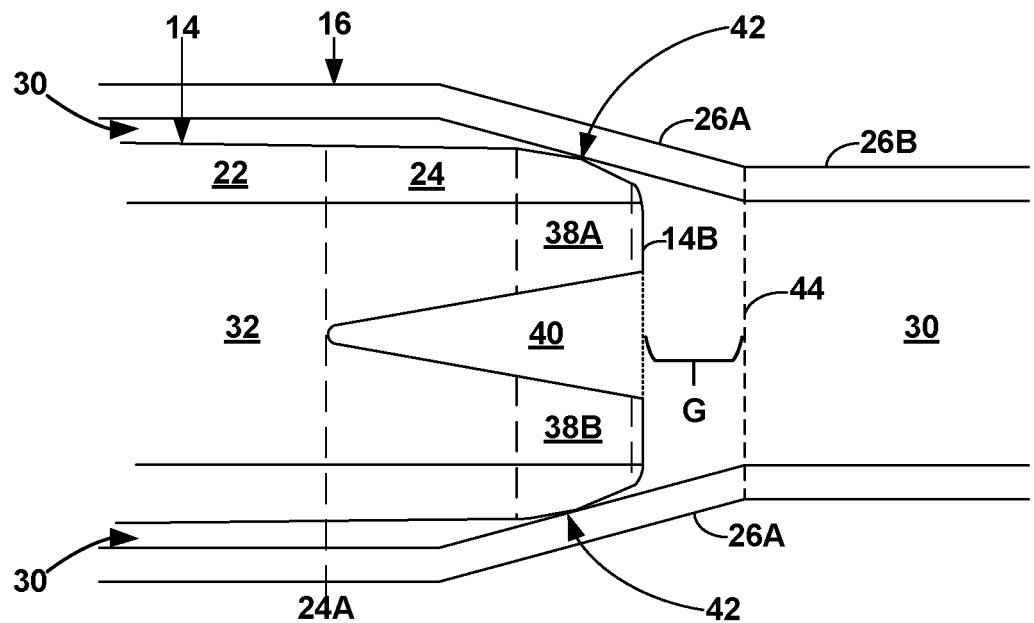
FIG. 4A is a cross-sectional view of a distal portion of the example introducer tool of FIGS. 2A-3 in an expanded configuration and partially inserted within an inner lumen of a delivery sheath.
Figure 4B:
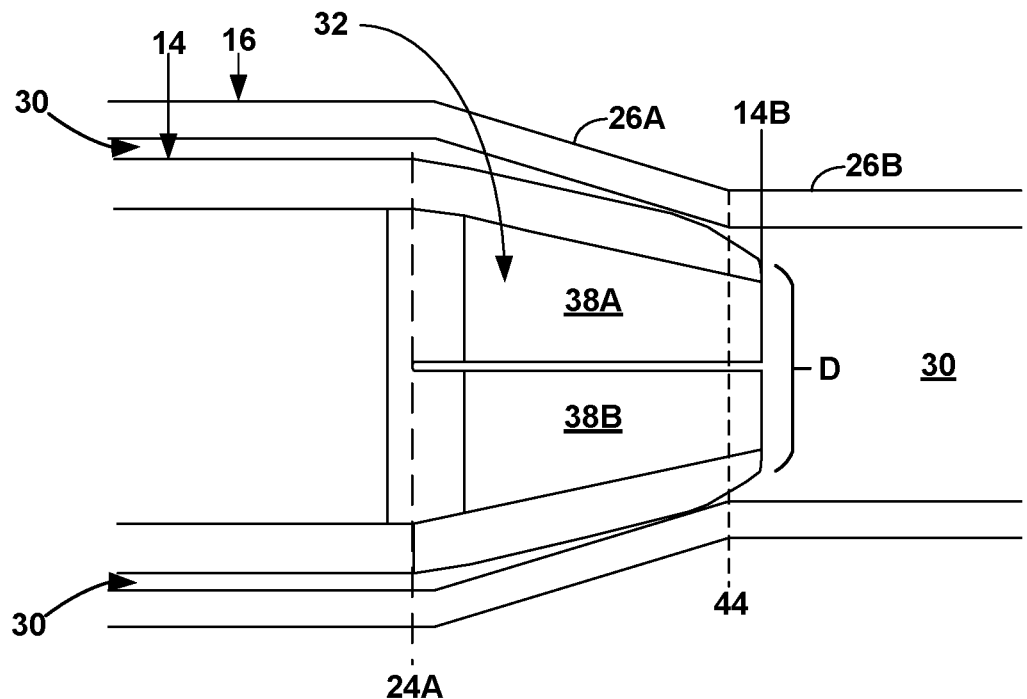
FIG. 4B is a cross-sectional view of a distal portion of the example introducer tool of FIG. 4A in a compressed configuration and fully inserted within the inner lumen of the delivery sheath.
Figure 5A:
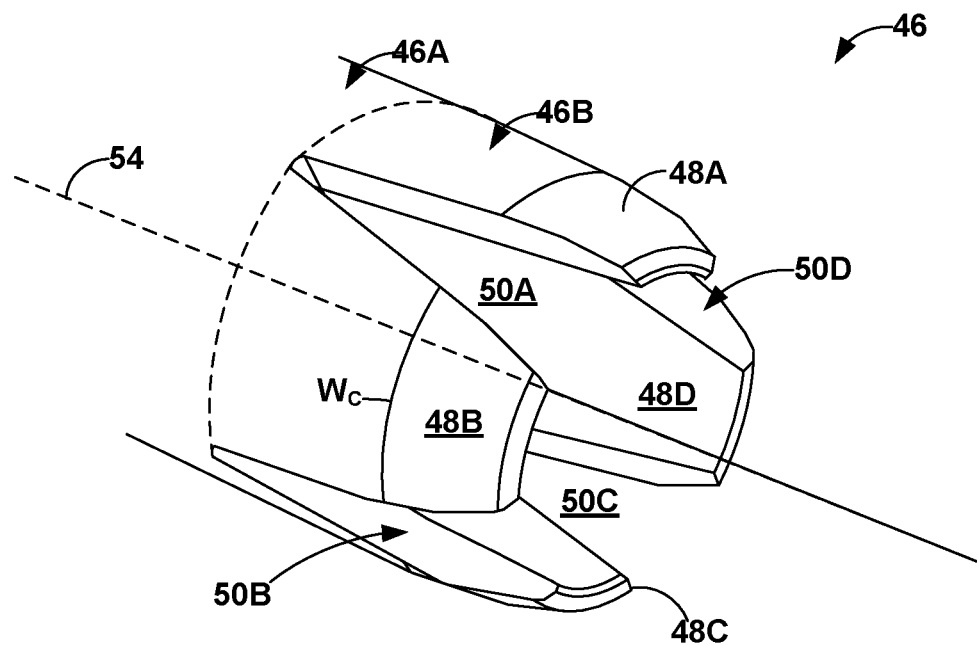
FIG. 5A is a perspective view of a distal portion of another example introducer tool in an expanded configuration.
Figure 5B:
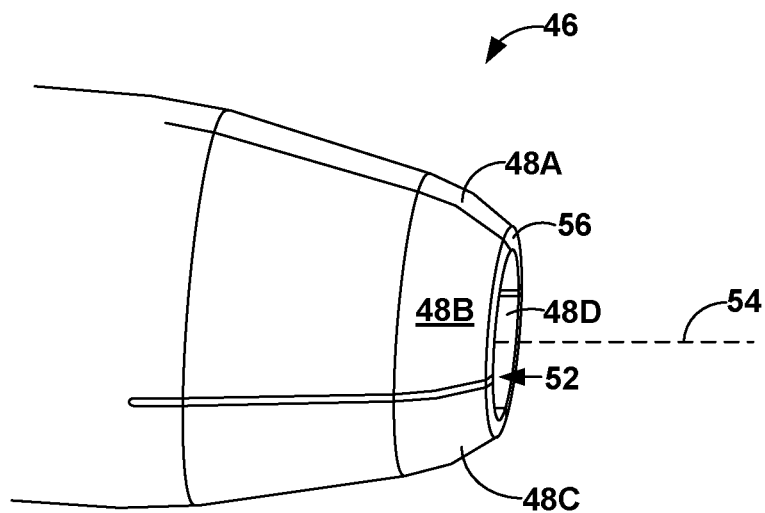
FIG. 5B is a perspective view of the distal portion of the introducer tool of FIG. 5A in a compressed configuration.

FIGS. 4A and 4B are schematic cross-sectional views illustrating an example technique for using the introducer tool 14 of FIGS. 1-3. As described above, the introducer tool 14, while in the expanded configuration shown in FIG. 4A, may be introduced into an inner sheath lumen 30 of the delivery sheath 16 until a distal portion of an exterior surface of the introducer tool 14 contacts an interior surface of a tapered sheath portion 26A of the delivery sheath 16, typically at some distance proximal to a proximal-most edge of a narrower distal sheath portion 26B of the delivery sheath 16. This contact causes the distal tool portion 24 to collapse into the compressed configuration shown in FIG. 4B.

FIG. 4A depicts the distal tool portion 24 of the introducer tool 14 in an expanded configuration while received within the inner sheath lumen 30 of the delivery sheath 16. Although not depicted in FIG. 4A, the expandable member 20 of the catheter 12 is received within the inner tool lumen 32 of the introducer tool 14.

In the expanded configuration depicted in FIG. 4A, the introducer tool 14 may be distally advanced into the inner sheath lumen 30 until a portion of the exterior surface of the introducer tool 14 contacts a portion of the interior surface of a tapered portion 26A of the delivery sheath 16, e.g., at the contact points 42 shown in FIG. 4A. As indicated above, the introducer tool 14 may define a rounded, tapered, or beveled exterior surface near the distal-most tool end 14B. Accordingly, the portion of the exterior surface of the introducer tool 14 that contacts the interior surface of the delivery sheath 16 at the contact points 42 may be located some distance proximal to the distal-most tool end 14B of the introducer tool 14.

At this point, in many cases, there exists a longitudinal gap "G" between the distal-most end 14B of the introducer tool 14 and a proximal edge 44 of a reduced-diameter distal sheath portion 26B of the delivery sheath 16. With some other introducer tools, while the catheter 12 is extended distally outward from the distal tool end 14B of the introducer tool 14 and into the reduced-diameter distal sheath portion 26B of the delivery sheath 16, the expandable member 20 of the catheter 12 (FIG. 1) may at least partially self-expand radially outward within the gap "G." The resulting friction between the expandable member 20 and the interior surface of the tapered sheath portion 26A of the delivery sheath 16 may require additional pushing force, e.g., applied to a proximal portion of the catheter 12, in order to compress the expandable member 20 and fully advance the catheter 12 into the sheath lumen 30 in the reduced-diameter distal sheath portion 26B of the delivery sheath 16.

The distal tool portion 24 of the introducer tool 14 is configured to collapse radially inward into the compressed configuration depicted in FIG. 4B. For instance, in response to a distal advancing force applied to a proximal portion of the introducer tool 14, the resulting pressure applied to the rounded or beveled exterior surface of the distal tool portion 24 of the introducer tool 14 at the contact points 42 (FIG. 4A) causes the axial extensions 38A, 38B to move radially inward, such as by hingedly bending, e.g., pivoting at or near the proximal-most edge 24A of the distal tool portion 24, such that the distal-most edges of the axial extensions 38 move radially inward. In this way, the introducer tool 14 collapses into the compressed configuration shown in FIG. 4B, having a reduced outer circumference and a reduced diameter "D" at the distal-most tool edge 14B of the introducer tool 14.

By collapsing radially inward into the compressed configuration, the distal tool portion 24 of the introducer tool 14 helps reduce a pushing force required to advance the catheter 12 into the inner sheath lumen 30 within the reduced-diameter distal sheath portion 26B of the delivery sheath 16. For example, while in the compressed configuration, the reduced outer perimeter (e.g., the circumference, in the case of a round cross-section) of the introducer tool 14 enables the introducer tool 14 to advance farther into the tapered sheath portion 26A of the delivery sheath 16, thereby reducing or (as shown in FIG. 4B) even eliminating the gap "G" (FIG. 4A) between the distal end 14B of the introducer tool 14 and the proximal edge 44 of the reduced-diameter distal sheath portion 26B of the delivery sheath 16. Accordingly, the introducer tool 14 reduces or eliminates the ability of the expandable member 20 of the catheter 12 to expand radially outward within the gap G before re-compressing radially inward within the reduced-diameter distal sheath portion 26B of the delivery sheath 16. The rounded or beveled exterior surface near the distal tool end 14B of the introducer tool 14 further helps to reduce friction between the introducer tool 14 and the delivery sheath 16. For instance, the beveled exterior surface may help the distal tool portion 24 of the introducer tool 14 to conform to the tapered interior surface of the delivery sheath 16 as the distal tool portion 24 collapses radially inward and the introducer tool 14 advances distally forward.

Although not depicted in FIG. 4B, when the expandable member 20 is retained within the inner lumen 32 of the distal tool portion 24 of the introducer tool 14 while the distal tool portion 24 collapses into the compressed configuration, the expandable member 20 likewise collapses radially inward or "necks down" into a compressed delivery configuration. While in the delivery configuration, the expandable member 20 is configured to more-easily advance into and through the inner sheath lumen 30 of the delivery sheath 16, particularly within the reduced-diameter distal sheath portion 26B of the delivery sheath 16.

With some other example introducer tools, in which the distal tool portion 24 does not compress radially inward, when the expandable member 20 of the catheter 12 is advanced distally outward from the distal tool end 14B and into the gap G, the expandable member 20 may contact an interior surface of the tapered sheath portion 26A of the delivery sheath 16. In some such examples, the catheter 12 may require significant additional pushing force to cause the expandable member 20 to neck down into the delivery configuration and advance distally forward into the narrower sheath portion 26B of the delivery sheath 16. In examples described herein, an outer maximum cross-sectional dimension (e.g., diameter) of the distal tool portion 24 of the introducer tool 14 may be reduced in order to advance distally closer to the narrower sheath portion 26B of the delivery sheath 16, thereby enabling a smoother transition of a collapsed expandable member 20 between the introducer tool 14 and the delivery sheath 16.

FIGS. 5A and 5B are perspective views of a distal portion of another example introducer tool 46, which is an example of the introducer tool 14 of FIGS. 1-4B, except for the differences noted herein. FIG. 5A depicts a distal tool portion 46B of the introducer tool 46 while in an expanded configuration, e.g., consistent with the examples described above, and FIG. 5B is a perspective view of the distal tool portion 46B of the introducer tool 46 while in a compressed configuration, consistent with the examples described above.

Unlike the introducer tool 14, which is depicted in FIGS. 1-4B as having two axial extensions 38A, 38B circumferentially separated by slits 40, the distal tool portion 46B of the introducer tool 46 includes four axial extensions 48A-48D (collectively, "axial extensions 48"). The axial extensions 48 are evenly distributed around an outer perimeter (e.g., a circumference) of the distal tool portion 46B of the introducer tool 46, e.g., around the longitudinal axis 54. In other examples, the axial extensions 48 may be unevenly distributed around the outer perimeter, such that the distal tool portion 46B of the introducer tool 46 is asymmetrical.

In the expanded configuration shown in FIG. 5A, every pair of adjacent axial extensions 48 is separated by a respective slit 50A-50D (collectively, "slits 50"). That is, edges of directly adjacent axial extensions 48 may define a respective slit 50. In the compressed configuration shown in FIG. 5B, the axial extensions 48 move radially inward toward each other until adjacent axial extensions 48 come into contact, thereby reducing the width of the slits 50 and, in some cases, closing the slits 50. In this compressed configuration, the axial extensions 48 collectively define a tapered distal tip of the introducer tool 46. Further, the distal-most edges of the axial extensions 48 collectively define a distal tool mouth 52 of the introducer tool 46. In the fully compressed configuration shown in FIG. 5B, the axial extensions 48 collectively form a substantially coherent inner perimeter of the distal tool mouth 52, such as a ring-shape or circular shape 56.

Similar to the slits 40 of FIGS. 1-4B, as illustrated in FIG. 5A, the slits 50 each define a generally triangular-prism-type shape. Accordingly, each axial extension 48, defined by the material of the introducer tool 46 located in between two circumferentially adjacent slits 50, defines a shape having a circumferential width "Wc" that tapers in a distal direction. Other-shaped slits may be used in other examples.

Figure 6:
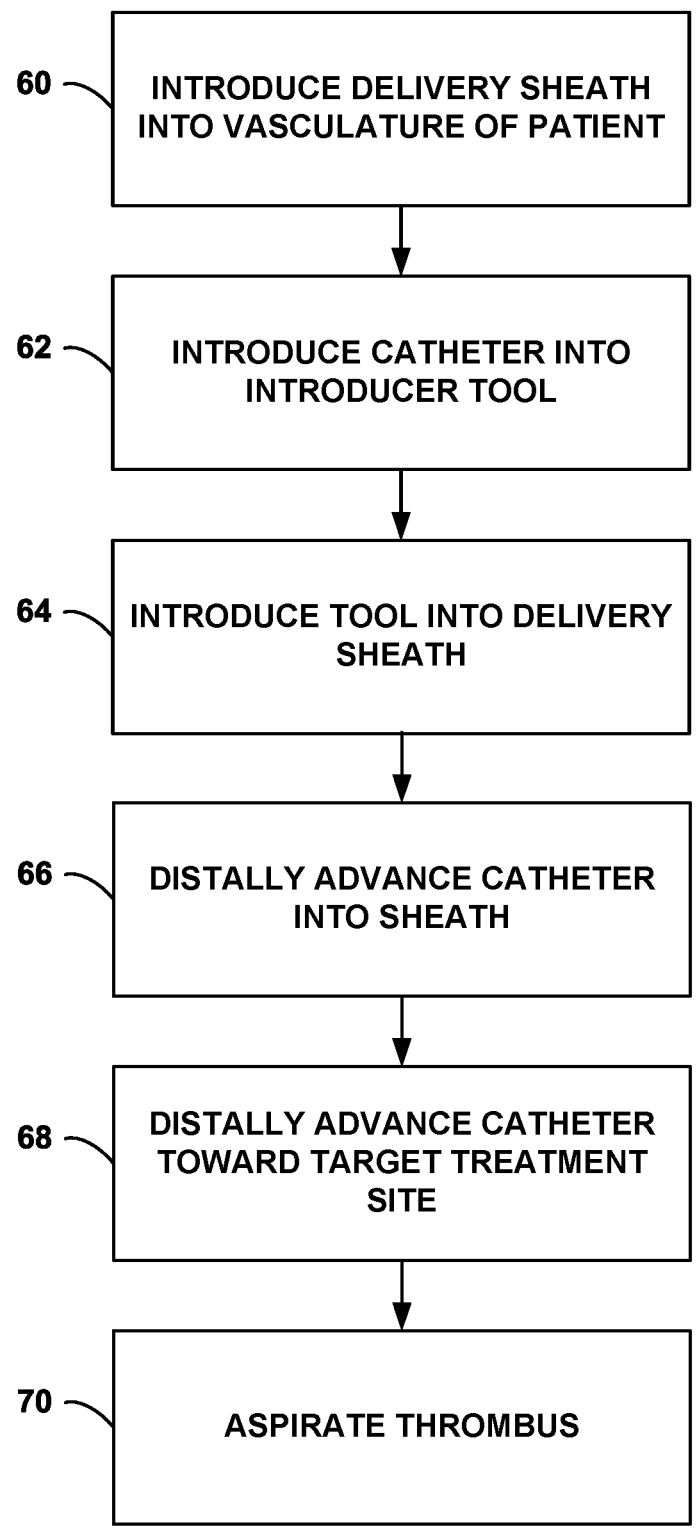
FIG. 6 is a flow diagram of an example method of using an introducer tool for a catheter, in accordance with techniques of this disclosure.

FIG. 6 is a flow diagram of an example method of aspiration using the medical assembly 10 of FIG. 1. The techniques of FIG. 6 are primarily described with reference to the introducer tool 14 of the medical assembly 10, however, in other examples, the technique may also be used with the introducer tool 46 of FIGS. 5A and 5B or other introducer tools including a collapsible distal tool portion, in accordance with examples described herein.

The method of FIG. 6 includes introducing, e.g., by a clinician, a delivery sheath 16 into vasculature of a patient and distally advancing the delivery sheath 16 through the patient's vasculature toward a target treatment site, e.g., toward a thrombus or other occlusive material (60).

In some examples, but not all examples, the method further includes introducing an expandable-mouth catheter 12 into an inner lumen 32 of an introducer tool 14 (62). In some such examples, the clinician may distally advance the catheter 12 until an expandable member 20 located at a distal portion of the catheter 12 is positioned within a variable-diameter distal tool portion 24 of the introducer tool 14. In other examples, the catheter 12 may be pre-loaded into the tool lumen 32 of the introducer tool 14, such as when the medical assembly 10, including the catheter 12 and the introducer tool 14, is packaged as a kit. For instance, the introducer tool 14 may form part of the medical device packaging in which the catheter 12 is packaged for transportation and storage. In some such instances, the introducer tool 14 may help protect the catheter 12 prior to use by a clinician.

The method further includes introducing the variable-diameter distal tool portion 24 of the introducer tool 14 into an inner sheath lumen 30 of the delivery sheath 16 (64), and distally advancing the introducer tool 14 through the inner sheath lumen 30 of the delivery sheath 16 until the distal tool portion 24 contacts an interior surface of a tapered sheath portion 26A of the delivery sheath 16. At this point, the pushing force applied to the introducer tool 14 causes a plurality of axial extensions 38 that make up the distal tool portion 24 of the introducer tool 14 to collapse radially inward, thereby narrowing the profile (e.g., diameter and circumference) of the distal tool portion 24 and enabling the distal tool portion 24 to advance farther into the tapered sheath portion 26A of the delivery sheath 16. In examples in which the expandable member 20 of the catheter 12 is positioned within the distal tool portion 24 of the introducer tool 14, the radially inward compression of the distal tool portion 24 additionally causes the expandable member 20 to occupy a lower-profile delivery configuration, e.g., by causing the expandable member 20 to "neck down," or contract radially inward, and in some examples, elongate in a longitudinal direction.

The method further includes advancing the catheter 12 (including the expandable member 20) distally outward from a distal tool mouth of the introducer tool 14 and into an inner lumen 30 of a narrower-diameter distal sheath portion 26B of the delivery sheath 16 (66). Once the expandable member 20 is positioned inside the narrower sheath lumen 30, the clinician may distally advance the catheter 12 through the delivery sheath 16 toward the target treatment site within the patient's vasculature (68).

In some examples, but not all examples, once the expandable member 20 of the catheter 12 is positioned within the inner sheath lumen 30 of the reduced-diameter distal sheath portion 26B of the delivery sheath 16, the introducer tool 14 may be proximally removed from the catheter 12. In some examples, the introducer tool 14 is configured to be longitudinally split and removed from around the catheter 12 in a lateral direction. For instance, the introducer tool 14 may be formed from a tearable material and/or may define a perforation configured to enable destructive removal of the introducer tool 14.

Once the expandable member 20 of the catheter 12 is positioned at the target treatment site, e.g., near the thrombus in the patient's vasculature, the clinician may then use the expandable-mouth catheter 12 to remove the occlusive material. For instance, the clinician may actuate an aspiration force within an inner lumen of the catheter 12, such that portions of the thrombus are aspirated into the expandable member 20 and proximally through the inner lumen of the catheter 12 (70). The catheter 12 may be removed from the patient's vasculature once the aspiration procedure is complete.

Various aspects of the disclosure have been described. These and other aspects are within the scope of the following examples and claims.

What is claimed is:

1. A medical assembly comprising:
    a catheter extending from a proximal end to a distal end and comprising an elongated catheter body and an expandable member, the expandable member located at a distal body portion of the elongated catheter body and defining a distal catheter mouth forming the distal end of the catheter and open to an inner lumen of the catheter, wherein the expandable member comprises a shape-memory material configured to enable the expandable member to self-expand radially outward to an expanded configuration to expand the distal catheter mouth to an expanded maximum cross-sectional dimension;
    a delivery sheath configured to be introduced into vasculature of a patient including a tapered portion and a distal sheath portion extending distally of the tapered portion, the delivery sheath defining a sheath inner lumen configured to receive the catheter; and
    an introducer tool configured to facilitate introduction of the catheter into the sheath inner lumen of the delivery sheath,
    wherein the introducer tool defines a tool inner lumen configured to receive the expandable member,
    wherein a distal tool portion of the introducer tool comprises a plurality of axial extensions extending between a tool proximal end and a tool distal end and configured to collapse radially inward toward a longitudinal axis of the introducer tool in response to a force applied by an interior surface of the tapered portion of the delivery sheath to the plurality of axial extensions, wherein when the introducer tool is received by the delivery sheath, at least the tapered portion of the delivery sheath contacts the plurality of axial extensions to prevent the tool proximal end from being advanced distally into the distal sheath portion, and wherein when the expandable member is positioned in the tool inner lumen, at least the distal tool portion is configured to compress the distal catheter mouth to a compressed maximum cross-sectional dimension smaller than the expanded maximum cross-sectional dimension.

2. The medical assembly of claim 1, wherein the axial extensions of the introducer tool are configured to collapse radially inward to reduce a distal profile of the introducer tool to enable the distal tool portion to advance farther into the tapered portion of the delivery sheath.

3. The medical assembly of claim 1, wherein the plurality of axial extensions are configured to collapse radially inward to compress the expandable member of the catheter into a delivery configuration while the expandable member is retained within the distal tool portion.

4. The medical assembly of claim 1, wherein each axial extension of the plurality of axial extensions defines a circumferential width that tapers in a distal direction.

5. The medical assembly of claim 1, wherein the plurality of axial extensions are separated by a plurality of slits.

6. The medical assembly of claim 5, wherein a distal-most portion of each slit of the plurality of slits defines a radial width of about 0.02 cm to about 0.25 cm, each radial width being measured in a direction perpendicular to the longitudinal axis of the introducer tool.

7. The medical assembly of claim 1, wherein each of the axial extensions defines an axial length of about 0.05 cm to about 1.00 cm, each axial length being measured in a direction parallel to the longitudinal axis of the introducer tool.

8. The medical assembly of claim 1, wherein the plurality of axial extensions comprises two axial extensions to four axial extensions.

9. The medical assembly of claim 1, wherein the plurality of axial extensions are configured to collapse radially inward into a compressed configuration, and wherein, while in the compressed configuration, sides of adjacent axial extensions of the plurality of axial extensions are configured contact each other.

10. The medical assembly of claim 9, wherein, while in the compressed configuration, the axial extensions collectively define a tapered distal tip of the introducer tool.

11. The medical assembly of claim 9, wherein, while in the compressed configuration, distal-most edges of the axial extensions collectively define a distal mouth of the introducer tool having a continuous outer perimeter.

12. The medical assembly of claim 1, wherein the introducer tool comprises an elongated tubular body that tapers in a distal direction.

13. The medical assembly of claim 1, wherein a distal-most exterior edge of each of the axial extensions is beveled.

14. The medical assembly of claim 1, wherein, to collapse radially inward, a distal-most end of each axial extension of the plurality of axial extensions pivots toward the longitudinal axis.

15. The medical assembly of claim 1, wherein the medical assembly comprises a kit comprising a plurality of different-sized introducer tools comprising the introducer tool.

16. The medical assembly of claim 1, wherein the introducer tool is configured to split to facilitate removal of the introducer tool from around from the catheter while the catheter is positioned within the delivery sheath.

17. The medical assembly of claim 16, wherein the introducer tool defines a groove or perforations extending longitudinally along the introducer tool, wherein the introducer tool is configured to split along the groove or the perforations.

18. A medical device assembly comprising:
a catheter extending from a proximal end to a distal end and comprising an expandable distal portion, the expandable distal portion defining a distal catheter mouth at the distal end of the catheter and open to an inner lumen of the catheter, wherein the inner lumen of the catheter is configured to receive fluid from a blood vessel of a patient via the distal catheter mouth, wherein the expandable distal portion comprises a shape-memory material configured to enable the expandable distal portion to self-expand radially outward to an expanded configuration to expand the distal catheter mouth to an expanded maximum cross-sectional dimension;
a delivery sheath configured to be introduced into vasculature of the patient including a tapered portion and a distal sheath portion extending distally of the tapered portion, the delivery sheath defining a sheath inner lumen configured to receive the catheter; and
an introducer tool configured to facilitate introduction of the expandable distal portion of the catheter into the delivery sheath, wherein the catheter is configured to be positioned within an inner tool lumen of the introducer tool, wherein a distal tool portion of the introducer tool comprises a plurality of axial extensions extending between a tool proximal end and a tool distal end and configured to collapse radially inward toward a longitudinal axis of the introducer tool in response to a force applied by an inner surface of the delivery sheath to an exterior surface of the plurality of axial extensions, wherein when the introducer tool is received by the delivery sheath, at least the tapered portion of the delivery sheath contacts the plurality of axial extensions to prevent the tool proximal end from being advanced distally into the distal sheath portion, and wherein when the expandable distal portion is positioned in the inner tool lumen, at least the distal tool portion is configured to compress the distal catheter mouth to a compressed maximum cross-sectional dimension smaller than the expanded maximum cross-sectional dimension.

19. The medical device assembly of claim 18, wherein the inner surface is positioned in the tapered portion.

* * * * *